| United States Patent [19] | [11] Patent Number: 4,701,444 |
|---|---|
| Segal et al. | [45] Date of Patent: Oct. 20, 1987 |

[54] TOPICAL PHARMACEUTICAL PREPARATIONS CONTAINING CHITIN SOLUBLE EXTRACT

[75] Inventors: Ester Segal, Tel-Aviv; Nurit Lehrer, Petah Tiqua, both of Israel

[73] Assignee: Ramot University Authority for Applied Research and Industrial Development LTD., Tel-Aviv, Israel

[21] Appl. No.: 645,111

[22] Filed: Aug. 28, 1984

[51] Int. Cl.⁴ .............................................. A61K 31/715
[52] U.S. Cl. .......................................... 514/55; 536/20
[58] Field of Search ............................... 536/20; 514/55

[56] References Cited

U.S. PATENT DOCUMENTS

| 3,847,897 | 11/1974 | Dunn et al. | 536/20 |
|---|---|---|---|
| 4,059,457 | 11/1977 | Austin | 536/20 |
| 4,447,562 | 5/1984 | Ivani | 536/20 |
| 4,532,321 | 7/1985 | Castle et al. | 536/20 |

FOREIGN PATENT DOCUMENTS 0027827  2/1984  Japan ................................. 514/55

*Primary Examiner*—J. R. Brown
*Assistant Examiner*—Elli Peselev
*Attorney, Agent, or Firm*—Fleit, Jacobson, Cohn & Price

[57] ABSTRACT

There are provided pharmaceutical compositions for topical application for preventing or at least substantially decreasing infections by yeasts of the genus Candida. These are based on a chitin soluble extract (CSE), which is obtained by the extraction of chitin by water with stirring. There are used ointments or lotions on a water-base.

4 Claims, No Drawings

TOPICAL PHARMACEUTICAL PREPARATIONS CONTAINING CHITIN SOLUBLE EXTRACT

FIELD OF THE INVENTION

The invention relates to pharmaceutical compositions for topical application for the prevention or for substantially decreasing infections by yeast and especially by Candida.

BACKGROUND OF THE INVENTION

The incidence of the infections by Candida, and especially by *C. albicans*, is a high one. Such infections exist as vaginal infections and as infections of the oral cavity, especially as denture stomatitis. There exists a wide variety of drugs for the treatment of such infections, which have various drawbacks. The present invention relates to compositions which substantially decrease adherence of Candida to epithelial cells.

SUMMARY OF THE INVENTION

The invention relates to pharmaceutical compositions for topical application to certain tissues, preventing adherence of Candida to such tissues, thereby substantially reducing the rate of infection by such yeasts. The active ingredient of the compositions is a substance defined herein as chitin soluble extract (CSE), prepared from commercially available chitin or from chitin extracted from *C. albicans*. The CSE derived from *C. albicans* is more active than the CSE derived from commercially available chitin. CSE can be advantageously prepared from various sources of chitin as set out in greater detail in the following experimental section.

Typically a suspension of commercially available chitin can be incubated in PBS, and the CSE can be obtained from the supernatant, or this supernatant can be used as such.

Candida chitin can be prepared from blastospores of *C. albicans* by boiling with hydrochloric acid, washing, boiling with a strong base. From the resulting chitin, CSE can be obtained.

The thus obtained CSE has a high biological activity. It prevents both in vitro and in vivo adherence of yeasts to epithelial cells. Thus, such preparations can be used to prevent vaginal infections by *C. albicans*, or for the prevention of denture stomatitis caused by such yeasts and for similar applications.

The activity of CSE derived from *C. albicans* is greater by a factor of about 10 to 20 times than that of CSE derived from commercially available chitin.

The pharmaceutical compositions of the invention are used in the form of water-based ointments, as lotions, as tampons imbued with the active substance etc. Generally a quantity of from 1 to 5 mg/ml of CSE is adequate, and small quantities of such compositions are sufficient to prevent infection by *C. albicans* and similar yeasts. The substance defined as CSE is water soluble with a solubility greater than 25 mg per ml water, it is heat stable and has a MW in excess of 10,000.

DESCRIPTION OF THE PREFERRED EMBODIMENT

Methodology

The active material (CSE) can be prepared from commercially available chitin as follows; and the thus obtained material was used for studies in vitro and in vivo.

Preparation of Chitin Soluble Extract (CSE)

A 20-percent chitin (Simga) suspension is PBS was incubated at room temperature for 5 h under constant shaking. The supernatant designated as CSE was then removed, dialysed overnight at 4° C. against sterile water and lyophilized. The yield of CSE in most of the preparations was 1-2 mg of lyophilized material per ml of supernatant.

Preparation of Chitin Soluble Extract (CSE) from Candida

Cultures of blastospores of *C. albicans*, harvested at the logarithmic growth phase were washed 3X with phosphate buffer (PBS), boiled 90 min with 1 N HCL, washed 3X with PBS, boiled with 1N NaOH for 90 min, washed 3X with PBS to a neutral pH and an insoluble pellet of chitin was obtained which was identified by the Morgan Elson test for identification of amino-sugars. This was agitated for 5 hours with water at room temperature. The product was lyophilized to obtain chitin powder. The yield was about 2 mg lyophilized material per ml of supernatant.

Induction of Experimental Canidal Vaginitis in Mice

The in vivo adherence of Candida to mucosal surfaces was studied in experimental vaginitis in mice. Six-week old female ICR mice (out-bred white mouse strain) were inoculated intravaginally with *C. albicans* (various concentrations; see "Results") using a wooden spatula. Mice were inoculated at different stages of the hormonal cycle: at oestrus, metoestrus, diestrus and proestrus stages. Duration of the oestrus cycle in rodents is 4-5 days.

Microscopic examination of Grain-stained or unstained vaginal smears taken from the inoculated mice was carried out in order to assess attachment of yeasts to exofoliated epithelial cells and to assay the development of hyphal elements at different times post-inoculation. In each smear, 100 epithelial cells were counted and epithelial cells with 20 or more attaching yeasts were considered adhering cells. Smears revealing at least 50 epithelial adhering cells and/or cells with hyphal elements on their surface were an indication of infection.

Vaginal discharges taken at various times post-inoculation were cultured on Sabouraud dextrose agar. Vaginal tissue section (5 μm) from infected mice were stained with Periodic acid Schiff (PAS) reagent and examined histopathologically.

RESULTS

Inhibition of In Vivo Adherence

Inhibition of in vivo adherence was achieved by treating the mice with various inhibitors which were administered topically in varying concentrations as vaginal rinses (50 μl, using Eppendorf tips) followed immediately by the inoculation of yeasts. Control animals were rinsed with PBS prior to inoculation of the yeasts and the control and test animals were compared for development of infection.

Effect of CSE on In Vitro Adherence

The addition of CSE (table 1) resulted in significant inhibition of the in vitro adherence of the yeasts. Lyophilizates prepared from the supernatant and added at a concentration of 2.5% W/V had an effect similar to that of the supernatant (table 1).

TABLE I

Effect of CSE, on in vitro adherence of *C. albicans* to human vaginal epithelial cells.

| Substance | Percentage of adherence alone (a) or in the presence of substance (b) | | Percentage of inhibition |
|---|---|---|---|
| | a | b | |
| Supernatant from chitin suspension | 45.3 ± 6.6 | 14.8 ± 6.1[1] | 67.4 |
| Lyophilizate of supernatant[2] | 41.3 ± 2.3 | 10.0 ± 3.6[1] | 51.6 |

[1]Adherence significantly lower than appropriate control = p 0.05 (Student t-test).
[2]Lyophilizate concentration 2.5% w/v.

TABLE 2

The effect of pretreatment of vaginal epithelial cells with chitin, CSE on adherence in vitro

| Treatment | Percentage of adherence | Percentage of inhibition |
|---|---|---|
| None | 42.5 ± 10.6 | 76.4 |
| Chitin[1] | 10.0 ± 5.6[3] | |
| None | 44.0 ± 0 | 72.7 |
| CSE[2] | 12.0 ± 5.6[3] | |

[1]Concentration 2.5% w/v.
[2]Concentration 2.5% w/v of lyophilized material.
[3]Percentage of adherence significantly lower (p < 0.05) than control (Student t'test).

Blocking of In Vivo Adherence of *C. albicans* to Murine Vaginal Mucosa

The next step in our study consisted of attempts to block the in vivo attachment of yeasts to vaginal mucosa in the murine experimental vaginitis model. Mice were pretreated topically with CSE and immediately inoculated with *C. albicans* organisms. The infection rate was assessed 24 hrs. after inoculation with yeasts and the results compared to those in the controls pretreated with PBS.

Nine experiments totalling 156 animals (Table 3) were performed. Of 74 mice pretreated with CSE, only 7 (9.0%) developed infection, compared to 36 (43.8%) out of 82 controls. The differences between infection rates of CSE-treated animals and those of controls were statistically significant (Student's t-test).

TABLE 3

Pretreatment of mice with CSE

| Experiment No. | Infection rate* | | | |
|---|---|---|---|---|
| | Control No. infected | | CSE No. infected | |
| | total | % | total | % |
| 1 | 3/10 | 30 | 1/10 | 10 |
| 2 | 5/10 | 50 | 1/10 | 10 |
| 3 | 5/10 | 50 | 2/10 | 20 |
| 4 | 3/8 | 37.5 | 0/8 | 0 |
| 5 | 4/8 | 50 | 0/8 | 0 |
| 6 | 3/8 | 37.5 | 1/8 | 12.5 |
| 7 | 4/10 | 40 | 1/10 | 10 |
| 8 | 5/10 | 50 | 1/10 | 10 |
| 9 | 4/8 | 50 | — | — |
| Total | 36/82 | 43.8 ± 7.7 | 7/74 | 9.0 ± 6.5** |

*Infection was evaluated 24 hrs. post-yeast inoculation by assaying the adherence of yeasts and hyphae to murine exfoliated vaginal epithelial cells (see "Methods").
**Infection rate significantly lower (p < 0.01) than control (student t-test).

As a control we also added a histological examination of vaginal tissues from mice pretreated with CSE or PBS and inoculated with yeasts. Sections from PBS-pretreated animals revealed fungal elements in the epithelium and an inflammatory cell reaction. The CSE-pretreated mice were devoid of such elements and the tissue appeared normal. No changes in the pattern of the effects of the various pretreatments were found during 5 days of followup.

Initial experiments to quantitate the dose-effect of the CSE by using lyophilizates prepared from supernatant of the chitin suspension indicated that the effect appeared to be dose-dependent (Table 4).

TABLE 4

Pretreatment of mice with various doses of lyophilizate of CSE

| | Infection 24 hrs. post-yeast inoculation* | | | |
|---|---|---|---|---|
| | Controls (PBS-treated) | Mice treated with CSE | | |
| | | Treatment 25 | dose 10 | (mg/ml) 1 |
| Inoculated | 6 | 6 | 6 | 6 |
| Infected | 3 | 0 | 0 | 1 |

*See Table 3.

The in vivo studies revealed that the chitin soluble extract was also inhibitory in vivo. The CSE effect was expressed both by blocking attachment to murine exfoliated vaginal epithelial cells and by preventing penetration into murine vaginal tissue. Such effects were obtained only when mice were pretreated with CSE prior to inoculation of the yeasts, and not when they were treated post-inoculation. This indicated that CSE leads to prevention of infection by blocking the attachment of yeasts to the host mucosal surfaces.

There were prepared lotions, water-base ointments and tampons impregnated with agqueous CSE extract. The usual concentration was about 1 to 3 mg/ml and the quantity applied was about 0.5 ml per day. This application substantially reduced infections by *C. albicans*, by preventing adherence of these to epithelial cells.

We claim:

1. A pharmaceutical composition used topically for preventing infection by, or for substantially decreasing the infection rate by yeasts of genus Candida comprising:
   chitin soluable extract in a suitable pharmaceutical carrier in a concentration of 1 to 10 mg of extract per milliliter of carrier.

2. A pharmaceutical composition according to claim 1, wherein said pharmaceutical carrier is selected from the group consisting of water-base ointment and lotion.

3. A composition according to claim 1, wherein the chitin soluble extract is derived from blastospores of *C. albicans*.

4. A method for treating vaginal infections caused by yeasts of the genus Candida comprising the step of
   applying intravaginally a pharmaceutical composition comprising chitin soluble extract in a suitable carrier, wherein said extract contains 1 to 10 mg chitin soluble extract per milliliter of pharmaceutical carrier.

* * * * *